US007166288B2

(12) United States Patent
Kirman et al.

(10) Patent No.: US 7,166,288 B2
(45) Date of Patent: Jan. 23, 2007

(54) USE OF INSULIN-LIKE GROWTH FACTOR BINDING PROTEIN 3 (IGF-BP3) FOR INHIBITION OF TUMOR GROWTH

(75) Inventors: Irena Kirman, Briarwood, NY (US); Richard L. Whelan, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 446 days.

(21) Appl. No.: 10/366,881

(22) Filed: Feb. 13, 2003

(65) Prior Publication Data
US 2004/0048794 A1 Mar. 11, 2004

Related U.S. Application Data

(60) Provisional application No. 60/357,000, filed on Feb. 13, 2002.

(51) Int. Cl.
*A61K 39/00* (2006.01)
*A61K 39/38* (2006.01)
(52) U.S. Cl. .................................. 424/184.1
(58) Field of Classification Search .............. 424/184.1
See application file for complete search history.

(56) References Cited

U.S. PATENT DOCUMENTS

| 5,407,913 | A | * | 4/1995 | Sommer et al. .............. 514/12 |
| 5,643,867 | A | | 7/1997 | Maack et al. |
| 5,840,673 | A | * | 11/1998 | Buckbinder et al. ........ 510/392 |
| 6,124,259 | A | | 9/2000 | Delmage et al. |
| 6,303,583 | B1 | * | 10/2001 | Kusunoki ..................... 514/50 |

FOREIGN PATENT DOCUMENTS

WO    WO 98/32022    *    7/1998

OTHER PUBLICATIONS

Taber's Cyclopedic Medical Dictionary, 1989, ed. by Clayton L. Thomas (F.A. Davis Company, Philadelphia, PA), p. 42.*
Eschwege and Dumas, 1995, Haematogenous dissemination of prostatic epithelial cells during radical prostatectomy, Lancet 346(8989):1528-1530.*
Sullivan et al., 2000, Regulation of expression of the multidrug resistance protein MRP1 by p53 in hujman prostate cancer cells, J. Clin. Invest. 105(9):1261-1267.*
Saltus, New Surgery called less invasive for prostate patients, The Boston Globe (Jan. 26, 2001), Boston, MA.*
Tortola et al., 1999, p53 and K-ras Gene Mutations Correlate With Tumor Aggressiveness But Are Not of Routine Prognostic Value in Colorectal Cancer, J. of Clin. Oncol. 17(5):1375-1381.*
Davenport et al., 1992, Insulin-Like Growth Factor-Binding Protein-3 Proteolysis Is Induced after Elective Surgery, J. of Clin. Endocrinol. 75(2):590-595.*

Allendorf et al., 1998, Increased tumor establishment and growth after open vs laproscopic bowel resection in mice, Surgical Endoscopy 12:1035-1038.*
Allendorf, J. D.; Bessler, M.; Horvath, K. D.; Marvin, M. R.; Laird, D. A.; Whelan, R. L. Increased tumor establishment and growth after open vs laparoscopic surgery in mice may be related to differences in postoperative T-cell function, Surg. Endosc. 1999, 13, 233-235 (Exhibit 1).
Allendorf, J. D.; Bessler, M.; Horvath, K. D.; Marvin, M. R.; Laird, D. A.; Whelan, R. L. Increased tumor establishment and growth after open vs laparoscopic bowel resection in mice. Surg. Endosc. 1998, 12, 1035-1038 (Exhibit 2).
Allendorf, J. D.; Bessler, M.; Kayton, M. L.; Oesterling, S. D.; Treat, M. R.; Nowygrod, R.; Whelan, R. L. Increased tumor establishment and growth after laparotomy vs laparoscopy in a murine model. Arch. Surg. 1995, 130, 6, 649-653 (Exhibit 3).
Bang, P.; Fielder, P. J. Human pregnancy serum contains at least two distinct proteolytic activities with the ability to degrade insulin-like growth factor binding protein-3. Endocrinology 1997, 138, 3912-3917 (Exhibit 4).
Cotterill, A. M.; Mendel, P.; Holly, J. M. P.; Timmins, A. G.; Camacho-Hübner, C.; Hughes, S. C. et al. The differential regulation of the circulating levels of the insulin-like growth factors and their binding proteins (IGFBP) 1, 2 and 3 after elective abdominal surgery. Clin. Endocrinol. 1996, 44, 91-101 (Exhibit 5).
Da Costa, M. L.; Redmond, P.; Bouchier-Hayes, D. J. The effect of laparotomy and laparoscopy on the establishment of spontaneous tumor metastases. Surgery 1998, 124, 516-525 (Exhibit 6).
Davenport, M. L.; Isley, W. L.; Pucilowska, J. B.; Pemberton, L. B.; Lyman, B.; Underwood, L. E.; Clemmons, D. R. Insulin-like growth factor-binding protein-3 proteolysis is induced after elective surgery. J. Clin. Endocrinol. Metab. 1992, 75, 590-595 (Exhibit 7).
Fanayan, S.; Firth, S. M.; Butt, A. J.; Baxter, R. C. Growth inhibition by insulin-like growth factor-binding protein-3 in T47D breast cancer cells requires transforming growth factor-beta (TGF-beta) and the type II TGF-beta receptor. J. Biol. Chem. 2000, 275, 39146-39151 (Exhibit 8).
Kansra, S.; Ewton, D. Z.; Wang, J.; Friedman, E. IGFBP-3 mediates TGF bet 1 proliferative response in colon cancer cells. Int. J. Cancer 2000, 87, 373-378 (Exhibit 9).
Lee, S. W.; Gleason, N. R.; Stapleton, G. S.; Zhai, C.; Huang, E. H.; Bessler, M.; Whelan, R. L. Increased platelet-derived growth factor (PDGF) release after laparotomy stimulates systemic tumor growth in mice. Surg. Endosc. 2001, 15, 981-985 (Exhibit 10).
Lee, S. W.; Gleason, N. R.; Southall, J. C.; Allendorf, J. D.; Blanco, I.; Huang, E. H et al. A serum-soluble factor(s) stimulates tumor growth following laparotomy in a murine model. Surg. Endosc. 2000, 14, 490-494 (Exhibit 11).

(Continued)

*Primary Examiner*—Jeffrey Siew
*Assistant Examiner*—Catherine Joyce
(74) *Attorney, Agent, or Firm*—John P. White; Cooper & Dunham LLP

(57) ABSTRACT

A method of inhibiting proliferation of cells associated with a tumor in a subject which comprises administering to the subject a tumor cell proliferation amount of IGF-BP3, thereby inhibiting proliferation of the cells. An improved surgical method which comprises surgically resecting a tumor from a subject and administering to the subject an amount of a protein effective to inhibit metastasis of any tumor cells released in the subject's blood circulation during the surgical resection of the tumor.

7 Claims, 5 Drawing Sheets

OTHER PUBLICATIONS

Lee, S. W.; Southall, J. C.; Allendorf, J. D.; Bessler, M.; Whelan, R. L. Tumor proliferative index is higher in mice undergoing laparotomy vs. $CO_2$ pneumoperitoneum. *Dis. Colon Rectum* 1999, 42, 477-481 (Exhibit 12).

Lee, S. W.; Gleason, N. R.; Ssenymanturo, K.; Woodring, J.; Bessler, M.; Whelan, R. L. Colon cancer tumor proliferative index is higher and tumor cell death rate is lower in mice undergoing laparotomy vs. insufflation. *Surg. Endosc.* 1998, 12, 514 (Exhibit 13).

MacDonald, R. G.; Schaffer, B. S.; Kang, I. J.; Hong, S. M.; Kim, E. J.; Park, J. H. Growth inhibition and differentiation of the human colon carcinoma cell line, Caco-2, by constitutive expression of insulin-like growth factor binding protein-3. *J. Gastroenterol. Hepatol.* 1999, 14, 72-78 (Exhibit 14).

Milsom, J. W.; Bohm, B.; Hammerhofer, K. A.; Fazio, V.; Steiger, E.; Elson, P. A prospective, randomized trial comparing laparoscopic versus conventional techiniques in colorectal cancer surgery: a preliminary report. *J. Am. Coil. Surg.* 1998, 187, 46-54 (Exhibit 15).

Murakami, K.; Matsuura, T.; Hasumura, S.; Nagamori, S.; Yamada, Y.; Saiki, I. Involvement of insulin-like growth factor binding protein-3 in the retinoic acid receptor-alpha-mediated inhibition of hepatocellular carcinoma cell proliferation. *Cancer Lett.* 2000, 151, 63-70 (Exhibit 16).

Pidgeon, G. P.; Harmey, J. H.; Kay, E.; Da Costa, M.; Redmond, H. P.; Bouchier-Hayes, D. J. The role of endotoxin/lipopolysaccharide in surgically induced tumour growth in a murine model of metastatic disease. *Br. J. Cancer* 1999, 81, 1311-1317 (Exhibit 17).

Rajah, R.; Valentinis, B.; Cohen, P. Insulin-like growth factor (IGF)-binding protein-3 induces apoptosis and mediates the effects of transforming growth factor-β1 on programmed cell death through a p53- and IGF-independent mechanism. *J. Biol. Chem.* 1997, 272, 12181-12188 (Exhibit 18).

Shiromizu, A.; Suematsu, T.; Yamaguchi, K; Shiraishi, N.; Adachi, Y.; Kitano, S. Effect of laparotomy and laparoscopy on the establishment of lung metastasis in a murine model. *Surgery* 2000, 128, 799-805 (Exhibit 19).

Southall, J. C.; Lee, S. W.; Allendorf, J. D.; Bessler, M.; Whelan, R. L. Colon adenocarcinoma and B-16 melanoma grow larger following laparotomy vs. pneumoperitoneum in a murine model. *Dis Colon Rectum* 1998, 41, 564-569 (Exhibit 20).

Taylor, L.D., et al. A transgenic mouse that expresses a diversity of human sequence heavy and light chain immunoglobulins. *Nucl. Acids Res.* 1992, 20, 6287-6295 (Exhibit 21).

Yu, H.; Rohan, T. Role of the Insulin-like Growth Factor family in cancer development and progression. *Review J. Natl. Cancer Inst.* 2000, 92, 1472-1489 (Exhibit 22).

Notification of Transmittal of the International Search Report issued by the International Searching Authority on Dec. 28, 2004 in connection with PCT International Application No. PCT/US03/04315, filed Feb. 13, 2003.

Oct. 21, 2005 Notification of Transmittal of International Preliminary Examination Report issued by the International Preliminary Examining Authority in connection with related International Application No. PCT/US03/04315.

* cited by examiner

USE OF INSULIN-LIKE GROWTH FACTOR BINDING PROTEIN 3 (IGF-BP3) FOR INHIBITION OF TUMOR GROWTH

This application claims benefit of U.S. Provisional Application No. 60/357,000, filed Feb. 13, 2002, now expired, the contents of which are hereby incorporated by reference.

Throughout this application, various publications are referenced by the first author's last name in parenthesis. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

The mainstay of treatment for the vast majority of intestinal and visceral malignancies has been "radical" resection of the tumor via laparotomy. In the past decade an alternative abdominal access method, namely laparoscopy, has been utilized, by some, for the curative resection of malignancies. This use of minimally invasive methods remains controversial because of the lack of long-term studies and concerns about port wound tumors. Early results from randomized trials comparing traditional to laparoscopic-assisted colon resection for cancer have shown that an adequate minimally invasive oncologic resection can be done (Milsom, J. W., et al.). Numerous experimental studies have demonstrated that laparotomy, when compared to $CO_2$ pneumoperitoneum or anesthesia alone, is associated with increased rates of tumor establishment and growth (Shiromizu, A., et al.; Allendorf, J. D., et al., 1995; Southall, J. C., et al.; Lee, S. W., et al., 1999). Similar results were noted after open and closed bowel resection (Allendorf, J. D., et al., 1998). Tumor cell proliferation was shown to be increased and apoptosis decreased after laparotomy in a murine study (Lee, S. W., et al., 1998). The mechanism of these tumor growth differences has also been investigated. Laparotomy related inhibition of immune function may account for some of the observed differences in tumor growth after surgery (Allendorf, J. D., et al., 1999; Da Costa, M. L., et al.). Laparotomy associated elevation of circulating active protein substances, such as VEGF may also play a role (Pidgeon, G. P., et al.). In an animal study that assessed the ability of pre- and postoperative mouse plasma to support tumor cells in vitro, significantly greater growth was noted in cultures to which post laparotomy serum (from postoperative days 2 and 4) had been added (Lee, S. W., et al., 2000). It was postulated that a surgery-related plasma factor accounted for the differences observed. In another study done with the same model, the factor was identified as platelet derived growth factor (PDGF) (Lee, S. W., et al., 2001)

SUMMARY OF THE INVENTION

The subject invention provides a method of inhibiting the proliferation of cells associated with a tumor in a subject which comprises administering to the subject a tumor cell proliferation amount of IGF-BP3, thereby inhibiting proliferation of the cells.

The subject invention further provides an improved surgical method which comprises surgically resecting a tumor from a subject and administering to the subject an amount of a protein effective to inhibit metastasis of any tumor cells released in the subject's blood circulation during the surgical resection of the tumor.

The improved surgical method comprises a surgical procedure on a subject and administering to the subject a prophylactically effective amount of IGF-BP3 to prevent proliferation of a tumor cell in the subject.

The subject invention also provides an article of manufacture comprising packaging material, IGF-BP3, and instructions for use of the IGF-BP3 in a surgical procedure.

DETAILED DESCRIPTION OF THE INVENTION

Figure 1:
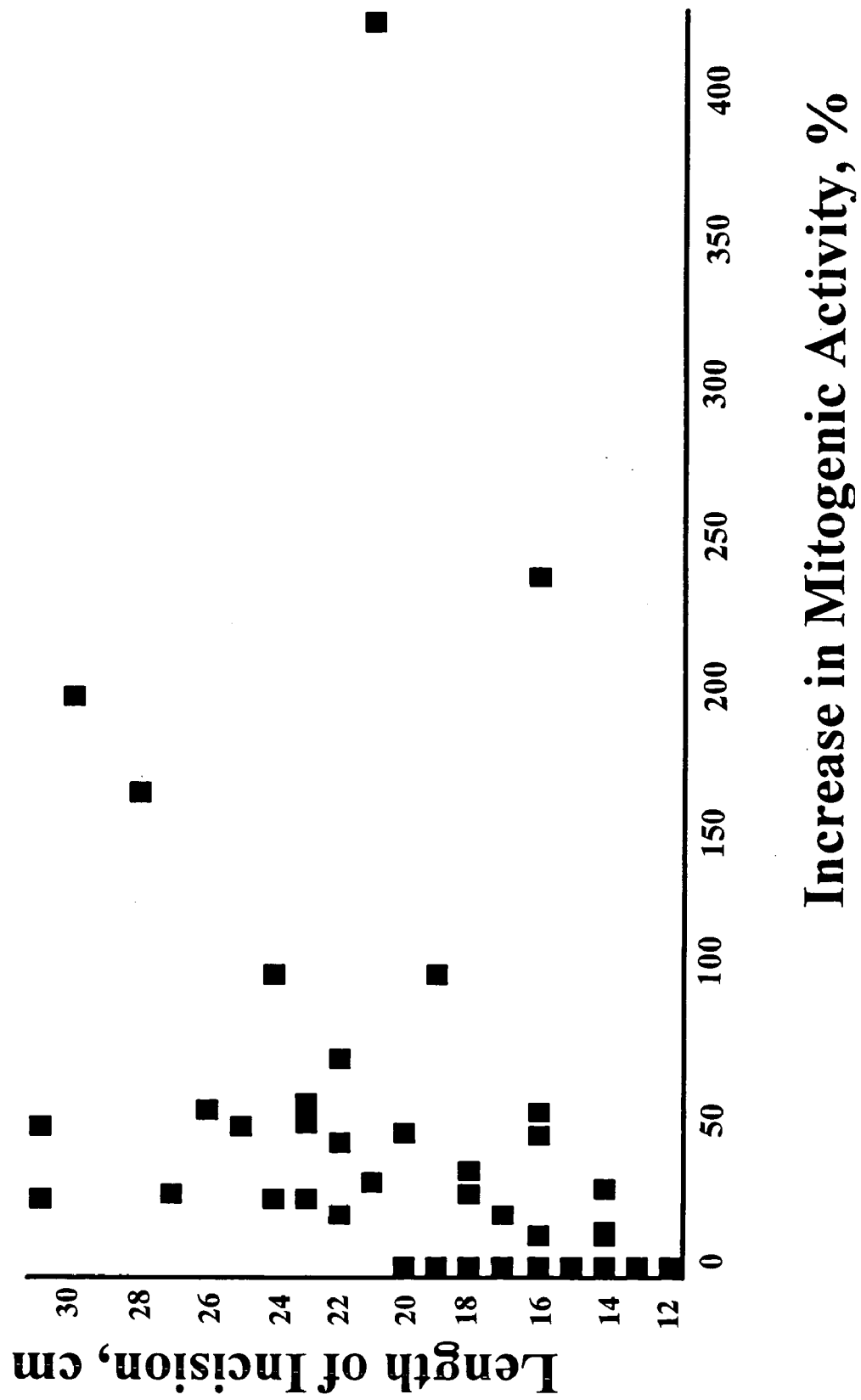
FIG. 1. Correlation between the Increase in OS Plasma Mitogenic Activity on POD1 and the Length of Incision. HT29 cells were incubated with 10% plasma from patients undergoing open surgery and BrdU incorporation test performed. A percentage increase in BrdU+ cells on POD1 versus preOP was calculated and plotted to the length of the incision.

The subject invention provides a method of inhibiting proliferation of cells associated with a tumor in a subject which comprises administering to the subject a tumor cell proliferation amount of IGF-BP3, thereby inhibiting proliferation of the cells.

This invention further provides an improved surgical method which comprises surgically resecting a tumor from a subject and administering to the subject an amount of a protein effective to inhibit metastasis of any tumor cells released in the subject's blood circulation during the surgical resection of the tumor.

The improved surgical method which comprises a surgical procedure on a subject and administering to the subject a prophylactically effective amount of IGF-BP3 to prevent proliferation of a tumor cell in the subject.

In an embodiment of the invention, the tumor is associated with colon cancer, prostate cancer, breast cancer or lung cancer. In specific embodiments, the subject is human and IGF-BF3 is recombinant IGF-BP3.

In another embodiment of the invention, the administration of IGF-BP3 is oral, intravenous or transdermal.

In an embodiment, the administration of IGF-BP3 is intravenous.

In a further embodiment of the invention, the surgical procedure is open abdominal surgery.

In an embodiment of the immediately preceding, the administration of IGF-BP3 is before start of the surgery.

In yet another embodiment of the preceding, the administration of IGF-BP3 is concurrent with the surgery.

In yet another embodiment of the preceding, the administration of IGF-BP3 is after the completion of the surgery.

In a specific embodiment of the preceding, the surgical procedure is colorectomy or gastric bypass.

The subject invention also provides an article of manufacture comprising packaging material, IGF-BP3, and instructions for use of the IGF-BP3 in a surgical procedure.

In an embodiment, the process of manufacturing the article comprises combining the packaging material, the IGF-BP3, and the instructions so as to manufacture the article.

The invention also provides the use of IGF-BP3 in the manufacture of a pharmaceutical composition for administering to a subject to inhibit proliferation of cells associated with a tumor.

In an embodiment of the preceding, IGF-BP3 is used in the manufacture of a pharmaceutical composition for administering to a subject before, during, or after a surgical procedure resecting a tumor from the subject in an amount effective to inhibit metastasis of any tumor cells released in the subject's blood circulation during the surgical resection of the tumor.

In a further embodiment of the preceding, IGF-BP3 is used in the manufacture of a pharmaceutical composition for administering to a subject before, during, or after a surgical procedure in an amount effective to prevent proliferation of a tumor cell in the subject.

This invention also provides an improved surgical use which comprises a surgical procedure on a subject and administering to the subject a prophylactically effective amount of IGF-BP3 to prevent proliferation of a tumor cell in the subject.

In an embodiment of the immediately preceding, IGF-BP3 is used for tumors associated with colon cancer, prostate cancer, breast cancer or lung cancer.

In a specific embodiment, recombinant IGF-BP3 is used for a human subject.

In an embodiment, the use of IGF-BP3 is via oral, intravenous or transdermal administration.

In an embodiment, the use of IGF-BP3 is via intravenous administration.

In one embodiment, the use of IGF-BP3 is in a surgical procedure wherein the surgical procedure is open abdominal surgery.

In a further embodiment, the use of IGF-BP3 is before start of the surgery.

In a yet a further embodiment, the use of IGF-BP3 is concurrent with the surgery.

In yet a further embodiment, the use of IGF-BP3 is after the completion of the surgery.

In a specific embodiment, the use of IGF-BP3 is for surgical procedure wherein the surgical procedure is colorectomy or gastric bypass.

The term "recombinant human antibody," as used herein, is intended to include all human antibodies that are prepared, expressed, created or isolated by recombinant means, such as antibodies expressed using a recombinant expression vector transsfected into a host cell, antibodies isolated from a recombinant, combinatorial human antibody library, antibodies isolated from an animal that is transgenic for human immunoglobulin genes or antibodies (Taylor, L. D., et al.) or antibodies prepared, expressed, created or isolated by any other means that involves splicing of human immunoglobulin gene sequences to other DNA sequences. Such recombinant human antibodies have variable and constant regions derived from human germline immunoglobulin sequences.

The antibodies and antibody-portions of the invention can be incorporated into pharmaceutical compositions suitable for administration to a subject. Typically, the pharmaceutical composition comprises an antibody (or antibody portion) of the invention and/or methotrexate and a pharmaceutically acceptable carrier. "Pharmaceutically acceptable carrier" includes any and all solvents, dispersion media, coatings, antibacterial and antifungal agents, isotonic and absorption delaying agents, and the like that are physiologically compatible and are suitable for administration to a subject. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The compositions of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular injection. In a particularly preferred embodiment, the antibody is administered by subcutaneous injection.

The antibodies and antibody-portions of the present invention can be administered by a variety of methods known in the art, although for many therapeutic applications, the preferred route/mode of administration is subcutaneous injection. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyethylene glycol (PEG), polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers and the like. To administer a compound of the invention by other than parenteral administration, it may be necessary to coat the compound with, or co-administer the compound with, a material to prevent its inactivation.

Experimental Details

Materials

Patients. Eighty-four patients (43 males and 42 females) that underwent either a colorectal resection or a gastric bypass for morbid obesity were included in this study. Forty-five patients underwent open surgery whereas 39 had minimally invasive procedures. Patients on corticosteroids, other immunosuppressive drugs, and those who had undergone chemotherapy or radiotherapy within 3 months of surgery were excluded from the study. Anesthesia was induced and maintained with propofol, succinyl choline and nitrous oxide. Additionally fentanyl and magnesium sulfate were given. The study was approved by the institutional IRB and informed consent was obtained from all patients.

TABLE 1

Indications for Surgery

| Indication | OS group, n (%) | LS group, n (%) |
| --- | --- | --- |
| Colorectal cancer | 20 (44) | 22 (56) |
| Morbid Obesity | 13 (29) | 8 (21) |
| Colorectal Adenoma | 8 (18) | 5 (13) |
| Diverticular Disease | 4 (9) | 4 (10) |

OS denotes Open Surgery
LS denotes Laparoscopic Surgery

TABLE 2

Accompanying Diseases in LS and OS Patients

| Accompanying Diseases | OS group, n (%) | LS group, n (%) |
| --- | --- | --- |
| Coronary artery disease, Hypertension | 14 (31) | 16 (41) |
| Chronic Obstructive Pulmonary Disease, Asthma | 5 (11) | 3 (8) |
| Diabetes | 4 (9) | 2 (5) |
| Past surgery | 5 (11) | 4 (10) |

The indications for surgery are provided in Table 1 whereas Table 2 concerns associated illnesses. The two groups were statistically similar in regards to indication and associated illnesses, age (overall groups and subgroups), and mean height and weight for each group. Furthermore, in regards to the colon cancer patients, there were no significant differences noted in final tumor stage, size of tumor, overall length of specimen, number of lymph nodes, or margins. There were no conversions in the laparoscopic group. None of the patients in either group received perioperative blood transfusions. The mean length of incision was 19.4±4.7 cm in the OS group and 5.0±2.1 cm in LS group.

Peripheral Blood Collection. Samples were collected in EDTA containing tubes pre-operatively and on post-operative days 1 and 3. Plasma was isolated by centrifugation soon after being drawn and stored at −80° C. until used.

Tumor Cell Line. The HT29 tumor, a human colonic adenocarcinoma cell line, was obtained from ATCC (Manassas, Va.) and maintained in complete DMEM medium (Cellgro, Herndon, Va.) with 10% fetal calf serum (FCS)(Cellgro). For the assay, HT29 cells were plated in 6-well plates, $2 \times 10^5$ cells/well in 2 ml of complete medium with FCS, and allowed to adhere. Cells were then washed 2 times with serum free DMEM medium and incubated for 48 hours with 10% human serum from the patients.

Biological Testing

5-Bromo-deoxyuridine (BrdU) Incorporation Assay. Two hours before the end of the incubation period, cells were pulsed with BrdU (BD Pharmingen, San Diego, Calif.), in a final concentration of 10 μM. Cells were then harvested by trypsinization, counted and washed with PBS 3 times. Cells were then fixed in 70% ethanol, washed again and denatured with 2M HCl. After neutralization with 0.1M sodium borate solution and 3 washes, cells were incubated with FITC labeled monoclonal antibody to BrdU (Caltag, Burlingame, Calif.), washed again and analyzed by flow cytometry using FACS Calibur (Becton Dickinson).

Total Cell Count. The total number of viable tumor cells in final cultures was determined by trypan blue dye (Cellgro) exclusion.

Detection of IGF-BP3 by Western Blot Analysis. Plasma, 5 μl diluted in Tris-Glycine loading buffer was electrophoresed on 18% Tris-Glycine pre-cast gels (Invitrogen, Carlsbad, Calif.) and transferred to a supported nitrocellulose membrane (Bio-Rad, Hercules, Calif.). Membranes were then blocked with 3% milk, incubated with a polyclonal biotinylated antibody to human IGF-BP3 (R&D Systems, Minneapolis, Minn.), washed with PBS, incubated with peroxidase labeled streptavidin (BD Pharmingen) and washed again. Membranes were developed using ECL reagent (Buckinghamshire, England) and an X-ray film.

Other IGF-BP3 Experiments. Neutralizing antibody to IGF-BP3 (human IGFBP3 specific goat IgG produced in goats immunized with purified, NSO-derived, recombinant IGFBP3): (R&D Systems, Minneapolis, Minn.) was added to the tumor cell cultures in final concentration 10 μg/ml. Recombinant purified human IGF-BP3 (rhIGF-BP3: Purified with Phenyl-Sepharose chromatography, Gel Filtration, IGFBP3 affinity chromatography, Reverse Phase HPLC; MW=47,000 Da) (Upstate Biotechnology, Lake Placid, N.Y.) was added to HT29 cells plated as previously described in final concentration 100–750 ng/ml in serum free medium. When added to wells containing 10% human serum, rhIGF-BP3 was added in final concentration 750 ng/ml.

Statistical Analysis. Data are expressed as means±SD. Wilcoxon's matched-pairs signed-ranks test and Spearman's correlation tests were used for statistical analysis.

Results

In Vitro Tumor Cell Proliferation

TABLE 3

Mitogenic Activity of Plasma from the OS and LS Groups

| Patient Groups | N | Age Yrs. | Plasma Mitogenic Activity | | | |
|---|---|---|---|---|---|---|
| | | | BrdU + cells, % | | Cells recovered from culture × 10⁵ | |
| | | | PreOP | POD1 | PreOP | POD1 |
| OS, All Patients | 45 | 56.6 ± 15.8 | 34.2 ± 17.9 | 42.4 ± 19.5** | 5.6 ± 1.6 | 7.0 ± 1.8** |
| OS, Colon Cancer[a] | 20 | 65.4 ± 12.6 | 30.5 ± 19.1 | 36.3 ± 18.0** | 5.4 ± 1.7 | 6.7 ± 1.8** |
| OS, Obesity | 13 | 43.1 ± 10.9 | 48.5 ± 7.8 | 56.7 ± 6.4** | 6.7 ± 0.6 | 7.8 ± 0.8** |
| OS, Colon Adenoma | 8 | 50.2 ± 15.0 | 23.7 ± 14.3 | 33.8 ± 22.3* | 4.3 ± 1.5 | 6.3 ± 3.0* |
| OS, Diverticulitis | 4 | 69.2 ± 6.2¶ | 26.7 ± 17.4 | 43.9 ± 29.1¶ | 5.7 ± 1.6 | 8.0 ± 1.7¶ |
| LS, All Patients | 39 | 59.8 ± 19.3 | 37.2 ± 18.1 | 36.6 ± 18.9 | 5.2 ± 1.3 | 5.1 ± 1.7 |
| LS, Colon Cancer[a] | 22 | 63.9 ± 17.6 | 32.6 ± 19.9 | 31.6 ± 18.4 | 4.9 ± 1.4 | 4.8 ± 1.7 |
| LS, Obesity | 8 | 38.9 ± 14.7 | 47.0 ± 14.9 | 42.1 ± 15.9 | 5.9 ± 1.3 | 5.8 ± 1.6 |
| LS, Colon Adenoma | 5 | 74.8 ± 8.3■ | 49.6 ± 8.7 | 56.5 ± 16.5¶ | 5.4 ± 1.0 | 5.8 ± 1.9¶ |
| LS, Diverticulitis | 4 | 60.8 ± 17.6¶ | 34.9 ± 17.5 | 36.3 ± 23.3¶ | 4.9 ± 0.7 | 5.0 ± 0.8¶ |

*P < 0.05;
**P < 0.005 PreOP versus POD1 using Wilcoxon's matched-pairs signed-ranks test.
■p < 0.05 compared to identical OS subgroup.
¶Insufficient n for a statistical analysis.
[a]Patients with colon cancer stage I–III were included; distribution of stages was comparable in OS and LS groups.

Open Surgery Group POD1 vs PreOp (Table3). For the overall group, a significantly higher proportion of tumor cells were BrdU+ in the cultures where POD1 OS plasma had been added (42.4±19.5%) when compared to the PreOP OS plasma results(34.2±17.9%, p<0.005). In regards to the total number of viable tumor cells found at the end of the incubation period, significantly more cells (7.0±1.8×10⁵) were noted in the POD1 OS wells than in the PreOP OS wells (5.6±1.6×10⁵, p<0.005) when the OS group as a whole was considered. Similarly significant differences for both proliferative parameters were noted when the colon cancer and the morbid obesity subgroups were considered separately. The other subgroups were too small to permit statistical analysis. The increase in mitogenic activity of POD1 OS plasma correlated with the length of surgical incision (p<0.01, r=0.58) (FIG. 1). Thirteen OS POD3 plasma samples were assessed. When considered together, no significant differences in BrdU incorporation or total cell count were noted when the POD3 and the PreOp plasma results were compared. However, when 5 patients with an incision equal or greater than 23 cm were considered, significantly increased HT29 proliferation was noted with the POD3 plasma when compared to the PreOP results (data not shown).

Laparoscopic Surgery Group. No differences in the percentage of BrdU+ cells or the total number of tumor cells were noted when the POD1 LS data were compared to the preOP LS data (Table 3). This was true for the overall group and for the 2 main subgroups where analysis was possible. A total of 14 POD3 LS plasma samples were similarly assessed. No differences in proliferation were noted when the POD3 LS and PreOp LS data were compared.

Plasma Factor Characterization Studies

Initial Studies. In a subset of patients, blood samples were collected in heparinized tubes in addition to the EDTA containing tubes. Although increased HT29 proliferation was noted with POD1 OS vs PreOP OS EDTA samples, no differences in tumor growth were noted when the heparinized plasma was tested (data not shown). In addition, heating of plasma to 99° C. eliminated the effect, which suggested that the factor(s) was a protein. We searched for a protein serum factor which could be stabilized by EDTA. Insulin-like growth factor binding protein 3 (IGF-BP3) was a likely candidate, because EDTA inhibits activity of IGF-BP3 specific serum protease, an enzyme that cleaves IGF-BP3 (Bang, P., et al.). In addition, surgery has been reported to induce IGF-BP3 protease activity (Davenport, M. L., et al.). Because the antibody in the available ELISA for IGF-BP3 reacts both with the intact protein (~40 kDa) and the biologically inert protein fragments, a Western Blot analysis was performed.

Figure 2:
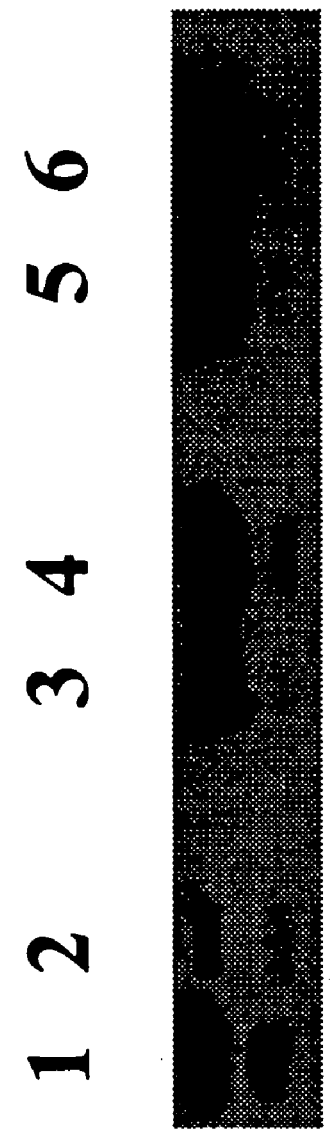
FIG. 2. IGF-BP3 Western Blots. Each pair of lanes is one patient's PreOP and POD1 results; Lanes 1 & 2 show an OS patient; Lanes 3 & 4 and 5 & 6, respectively, are 2 LS patients' results. IGF-BP3 was notably decreased in the OS patient on POD1 (Lane 2) versus PreOP (Lane 1), but not in the LS patients (Lanes 4 and 6 vs. Lanes 3 and 5).

Western Blot Analysis. PreOP and POD1 plasma levels of IGF-BP3 were determined for all patients. In 5 of 45 OS patients (11.1%) and 6 of 39 LS patients (15.4%), IGF-BP3 was not detected in any of the samples. For the remaining patients, a decrease in plasma IGF-BP3 on POD1 when compared to PreOP levels was noted in 80.9% of OS patients and in 16.7% of LS patients. OS patients with preserved post-operative levels of circulating IGF-BP3 had shorter incisions (<23 cm). Representative Western Blot results are displayed in FIG. 2.

Figure 3:
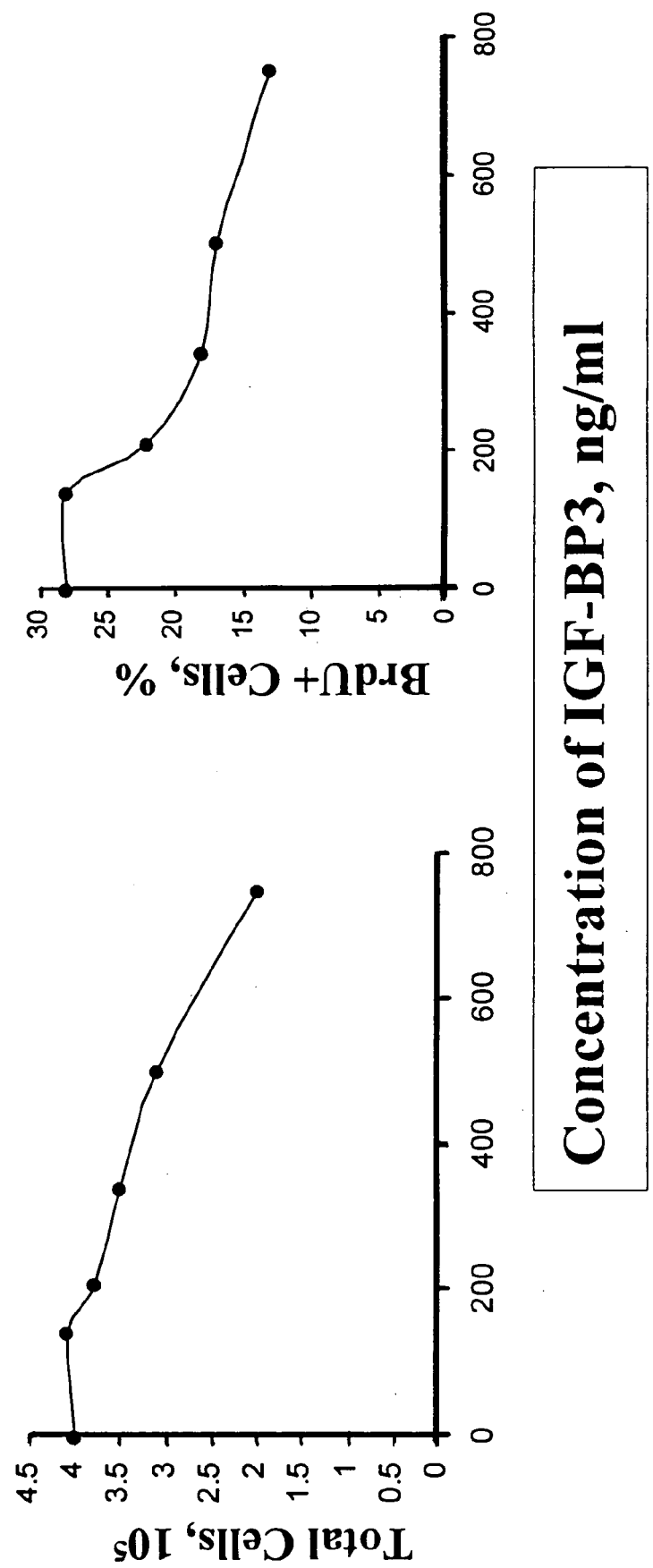
FIG. 3. Direct Inhibitory Effect of IGF-BP3 on Growth of. Colon Cancer Cells. HT29 cells were plated in serum free conditions with IGF-BP3 in various concentrations. The resulting number of recovered cells (left) and the percentage of BrdU+ cells in cultures decreased with increasing concentrations of IGF-BP3.

IGF-BP3 Effect on HT 29 Growth. To test whether IGF-BP3 directly affects HT29 growth, human recombinant IGF-BP3 (rhIGF-BP3) was added to serum free cultures of HT29 cells (FIG. 3). RhIGF-BP3 had an inhibitory effect on HT29 cell proliferation in the concentration range of 200–750 ng/ml; higher concentrations have not been tested. IGF-BP3 concentrations lower than 200 ng/ml did not have an impact on cell proliferation.

RhIGF-BP3 was added to POD1 OS plasma samples (n=6) at concentration of 750 ng/ml and HT29 proliferation assessed.

Figure 4:
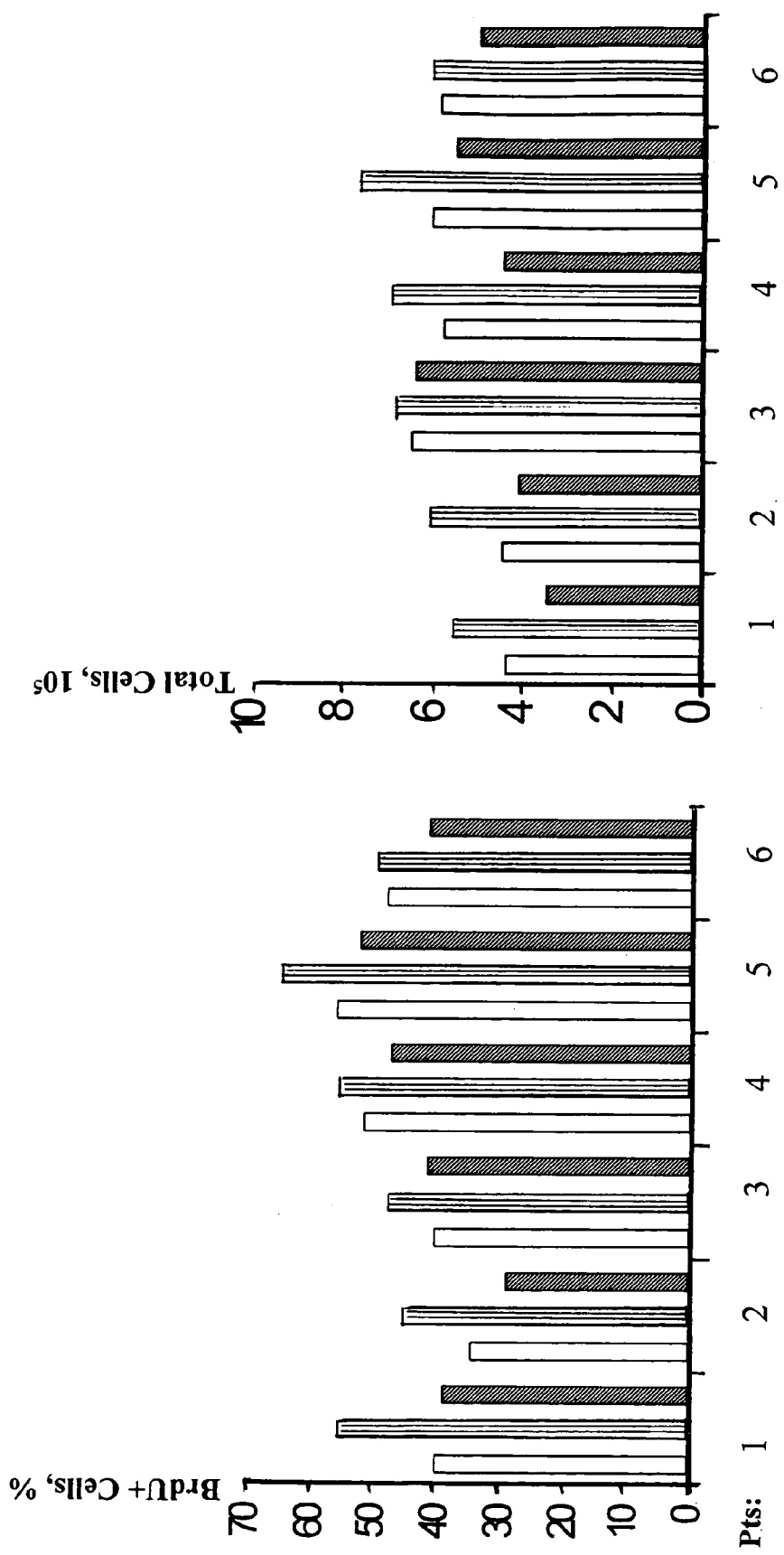
FIG. 4. Neutralization of the Mitogenic Effect. Each triplet displays one patient's results (unshaded bars, PreOP results; black bars, POD1 results; crosshatched bars, rhIG-FBP3 supplemented POD1 results). Recombinant human IGF-BP3 was added to cell cultures containing 10% POD1 OS plasma. The percentage of BrdU+ cells and the total cell count were decreased in supplemented wells (p<0.05 vs. PreOp Plasma) compared to results with POD1 plasma alone (closed). RhIGF-BP3 POD1 OS plasma vs. PreOP OS plasma, no difference noted.

Significantly less proliferation, as judged by both BrdU assay and cell counts, was noted in the rhIGF-BP3 augmented wells (FIG. 4) when compared to POD1 OS plasma results. There was no significant difference between the supplemented POD1 and the PreOP OS plasma results.

Figure 5:
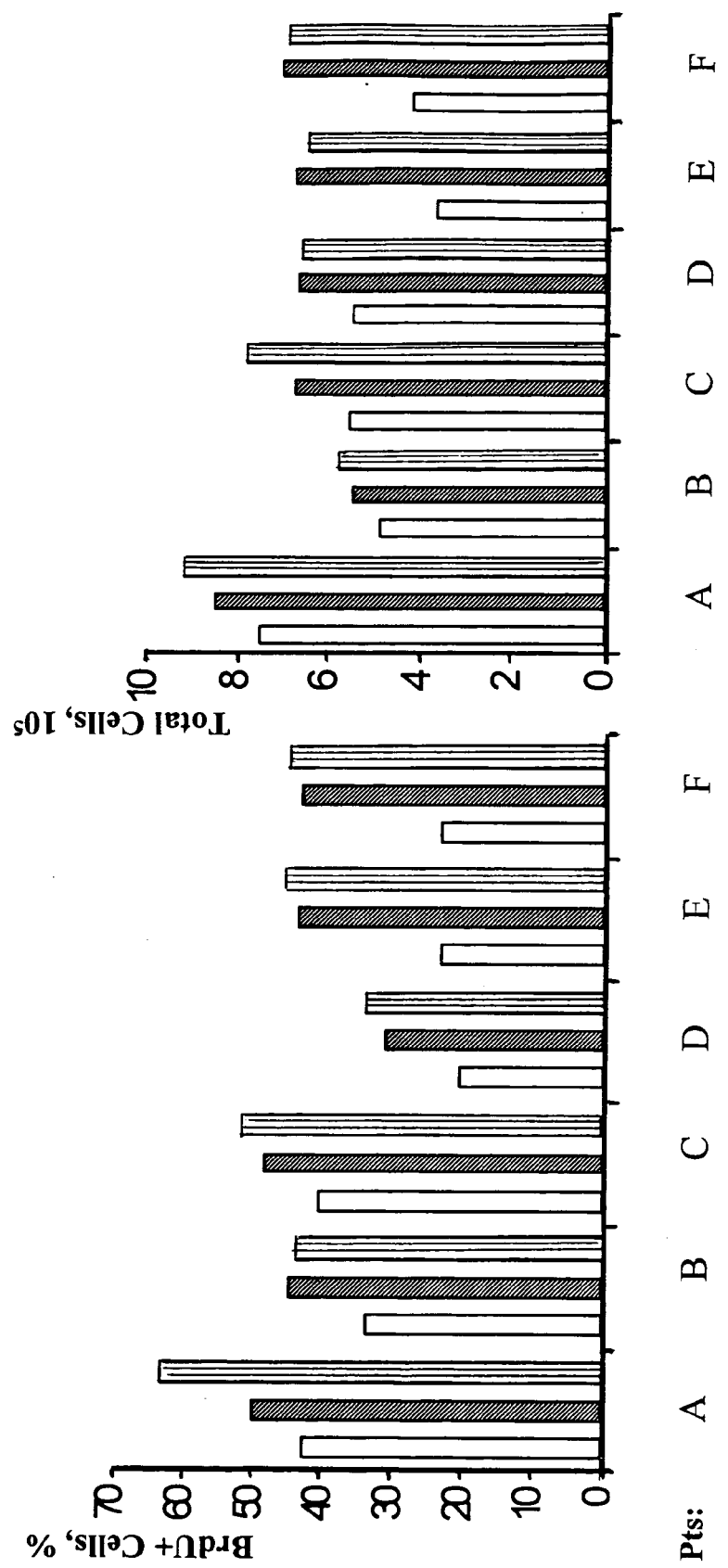
FIG. 5. Impact of Anti-IGFBP3 Antibody on the Mitogenic Effect of PreOP OS Plasma. Each triplet displays one patient's results (unshaded bars, PreOP results; crosshatched bars, ab+PreOp Plasma results; black bars, POD1 OS results). Neutralizing antibody to IGF-BP3 was added to wells containing PreOP OS plasma (concentration per well 10 μg/ml). HT29 proliferation (counts and BrdU incorporation) was significantly higher in antibody supplemented wells when compared to PreOP OS plasma results(p<0.05). The addition of antibody raised PreOp Plasma associated HT29 proliferation to levels observed with the POD1 OS plasma.

Impact of Neutralizing Antibody to IGF-BP3. Anti-IGF-BP3 antibody was added to PreOP OS plasma and HT29 proliferation assessed (n=6). Both BrdU and cell count results demonstrated significantly increased proliferation for the antibody supplemented group when compared to the PreOP plasma results (p<0.05). The anti-IGF-BP3 results were similar to those noted with the POD1 OS plasma (FIG. 5).

DISCUSSION

The present human study was undertaken to determine if major open and closed abdominal surgery had a similar effect on human plasma mitogenic activity for colon cancer cells. In a murine model, open surgery induced an increase in serum mitogenic activity and platelet-derived growth factor was thought to be the responsible protein (Lee, S. W. et al., 2001). The purpose of this human study was to determine if major abdominal surgery carried out via open or laparoscopic means was associated with alterations in the composition of plasma such that in vitro tumor growth would be enhanced. If such an effect was indeed observed, it was our hope to identify the responsible factor(s).

The results suggest that post-op day 1 plasma from open surgery patients enhances in vitro tumor growth and that the increased proliferation correlated directly with the length of the incision. Post-operative plasma from laparoscopic surgery patients did not have this effect. Increased growth was noted after both open colorectomy and gastric bypass and, therefore, does not appear to be related to the organ being operated on or to the presence of a malignancy. Although not randomized, close scrutiny of the open and closed groups in regards to demographics, associated illnesses, body habitus, indication, and pathology results (for tumors) suggested the two groups were similar. Of note, proliferation studies of the POD3 plasma, carried out on a fraction of the study patients, suggested that the tumor stimulatory effect is lost in all but those open patients with incisions equal or greater than 23 cm.

Plasma from laparotomized mice has been shown to stimulate in vitro tumor growth when compared to results with preoperative plasma. This study assessed the effect of plasma from patients that underwent major open (OS) or laparoscopic surgery (LS) on in vitro tumor cell growth. Eighty-four patients undergoing major abdominal surgery were studied (45 OS, 39 LS). Peripheral blood was collected preoperatively (PreOP) and on days 1(POD1) and 3(POD3) after surgery. HT29 human colon cancer cells were plated with samples of the plasma.

Proliferation was assessed via cell counts and the BrdU incorporation assay. IGF-BP3 (insulin-like growth factor binding protein 3) was detected in plasma via Western Blot analysis. Increased mitogenic activity was noted in POD1 OS plasma when compared to PreOP OS plasma results (p<0.005). This increase correlated with the length of incision (r=0.58, P<0.01). No differences were noted when the PreOP LS and POD1 LS results were compared or for any of the POD3 vs PreOP comparisons. Hence, major open surgery is associated with alterations in plasma composition that promote HT29 tumor cell proliferation in vitro. As shown, this effect was due, at least in part, to surgery-related depletion of IGF-BP3 in peripheral blood.

Plasma from patients undergoing major open surgery stimulates in vitro tumor growth. Lower IGF-BP3 levels may, in part, account for this change. Plasma from mice undergoing laparotomy has been shown to stimulate in vitro tumor growth. The goals of this study were to determine the effect of plasma from patients that underwent major open (OS) or laparoscopic surgery (LS) on in vitro tumor growth and, if surgery-related differences were noted, to identify the responsible factor(s). Materials: A total of 58 patients undergoing major abdominal surgery were studied (34 OS and 24 LS patients). Peripheral blood was collected in heparinized and EDTA tubes before surgery (PreOP) and on days 1(POD1) and 3(POD3) after surgery. Plasma was obtained by centrifugation and stored at −70° C.

Proliferation Assay: HT29 human colon cancer cells were plated with 10% human serum from the patients. The BrdU cell proliferation assay was used. IGF-BP3 (insulin-like growth factor binding protein 3) was detected in plasma by Western Blot Analysis using specific antibody. Statistical Analysis was performed using paired Student's test and Pearson correlation coefficient. [P value of 0.05 or less was considered statistically significant.]

Increased mitogenic activity was noted with the POD1 OS plasma (41.4±20.4% BrdU+ cells) when compared to results with the PreOP OS plasma (32.5%±17.9%, p<0.01). This increase correlated with the length of incision (r=0.328, P=0.036). No difference in mitogenic activity was noted when the LS PreOP and the LS POD1 results were compared (32.6±20.7% vs 31.7±20.8%, respectively). [No differences were noted when POD3 and PreOp results were compared for either the OS and LS groups.] OS associated stimulation of HT29 cell growth was stronger with EDTA than with heparinized plasma. We searched for a serum factor that might be stabilized by EDTA. EDTA blocks IGF-BP3-related plasma proteolytic activity. Via Western Blot analysis, less IGF-BP3 was noted in the POD1 plasma samples associated with higher mitogenic activity. Purified IGF-BP3 at a concentration 500 ng/ml and higher appeared to inhibit HT29 proliferation, while addition of IGF-BP3 neutralizing antibody to PreOP plasma increased its mitogenic activity to the level of POD1 plasma. Major open surgery appears to enhance the ability of human plasma to promote HT29 tumor cell proliferation in vitro. This effect may be due, in part, to depletion of IGF-BP3 in peripheral blood following open surgery.

Having demonstrated the effect we next sought to identify the responsible factor(s). Serum PDGF β levels were determined via ELISA, however, no differences were noted (data not provided) in either group. For the reasons stated, IGF-BP3 was a reasonable candidate. The Western Blot findings and the results of the studies that supplemented with rhIGF-BP3 or anti-IGF-BP3 strongly suggest that IGF-BP3 is the responsible factor. An open surgery-related decrease in IGF-BP3 levels, most likely, accounts, in large part, for the in vitro tumor growth differences noted with POD1 Open surgery plasma. It has previously been shown that major open abdominal surgery induces proteolysis of circulating IGF-BP3 (Cotterill, A. M., et al.).

Intact IGF-BP3 can influence tumor growth via 2 mechanisms. First, it can bind circulating IGF-I, a well known growth factor, and thus limit IGF-I related stimulatory effects (Yu, H., et al.). Secondly, IGF-BP3 itself can deter proliferation directly by inducing tumor cell apoptosis. This direct effect has been documented for prostate cancer (Rajah, R., et al.), breast cancer (Fanayan, S., et al.) and hepatocellular carcinoma cells (Murakami, K., et al.). Interestingly, IGF-BP3's effect on colon cancer cells is less clear; one study suggested it was inhibitory (MacDonald, R. G., et al.) while another reported stimulatory effects (Kansra, S., et al.). In this study, the HT29 colon cell line was shown to be inhibited by IGF-BP3.

The possible implications of these results are far reaching. For the first time, in humans, the choice of surgical approach has been associated with host alterations that may increase the chances that tumor cells in the blood will survive and form a metastases. Thus, IGF-BP3 replacement in open cancer patients or supplementation in closed surgery patients should lower the risk of tumor recurrence.

Insulin-like growth factor binding protein 3 (IGF-BP3) is a serum protein that can exert an inhibitory effect on the growth of tumor cells via 2 major mechanisms: 1) it binds a major cell growth factor, insulin-like growth factor 1 (IGF-1) and 2) it directly inhibits tumor cell growth. The inhibitory effect of IGF-BP3 has been demonstrated for prostate, breast, and lung cancer. We have shown that high doses of IGF-BP3 also directly inhibits colon cancer cell growth in vitro.

In the described study, patients that underwent major open surgery (cancer and non-cancer patients) were noted to have reduced levels of IGF-BP3 shortly after surgery. We found that plasma from open surgery patients collected on postoperative day 1 stimulated in vitro tumor growth of colon cancer cells when compared to results obtained with their preoperative plasma samples. Addition of IGF-BP3 neutralizing antibody to preoperative plasma resulted in accelerated tumor cell growth to the same degree as observed with postoperative plasma. In addition, supplementing the postoperative day 1 plasma with recombinant IGF-BP3 eliminated the tumor cell stimulation that had been noted with the "raw" postoperative day 1 plasma. Thus, we propose inhibition of recurrent tumor and/or metastatic tumor formation via perioperative administration of insulin-like growth factor binding protein 3 in cancer patients (all types of cancer) undergoing major surgery via a traditional open (a single lengthy incision) surgical approach.

The surgical resection of cancers is associated with the release of tumor cells into the circulation in a significant proportion of patients. These blood borne tumor cells may give rise to distant metastases. The chances that a circulating tumor cell will successfully form a metastases, regardless of the cancer type, in a patient undergoing an open surgery will be smaller if immediately after surgery the patient receives one of several injections of IGF-BP3.

Prior to our study, it was not known that open surgery induces the partial depletion of circulating plasma IGF-BP3 and that the depleted postoperative plasma stimulates cancer cell growth. Also, our study demonstrates that a similar effect can be achieved by adding IGF-BP3 neutralizing antibody to the preoperative plasma. Our study also shows that higher concentrations of recombinant IGF-BP3 improve the inhibitory effect for, e.g., colon cancer cells.

REFERENCES

Allendorf, J. D.; Bessler, M.; Horvath, K. D.; Marvin, M. R.; Laird, D. A.; Whelan, R. L. Increased tumor establishment and growth after open vs laparoscopic surgery in mice may be related to differences in postoperative T-cell function. Surg. Endosc. 1999, 13, 233–235.

Allendorf, J. D.; Bessler, M.; Horvath, K. D.; Marvin, M. R.; Laird, D. A.; Whelan, R. L. Increased tumor establishment and growth after open vs laparoscopic bowel resection in mice. Surg. Endosc. 1998, 12, 1035–1038.

Allendorf, J. D.; Bessler, M.; Kayton, M. L.; Oesterling, S. D.; Treat, M. R.; Nowygrod, R.; Whelan, R. L. Increased tumor establishment and growth after laparotomy vs laparoscopy in a murine model. Arch. Surg. 1995, 130, 6, 649–653.

Bang, P.; Fielder, P. J. Human pregnancy serum contains at least two distinct proteolytic activities with the ability to degrade insulin-like growth factor binding protein-3. Endocrinology 1997, 138, 3912–3917.

Cotterill, A. M.; Mendel, P.; Holly, J. M. P.; Timmins, A. G.; Camacho-Hübner, C.; Hughes, S. C. et al. The differential regulation of the circulating levels of the insulin-like growth factors and their binding proteins (IGFBP) 1, 2 and 3 after elective abdominal surgery. Clin. Endocrinol. 1996, 44, 91–101.

Da Costa, M. L.; Redmond, P.; Bouchier-Hayes, D. J. The effect of laparotomy and laparoscopy on the establishment of spontaneous tumor metastases. Surgery 1998, 124, 516–525.

Davenport, M. L.; Isley, W. L.; Pucilowska, J. B.; Pemberton, L. B.; Lyman, B.; Underwood, L. E.; Clemmons, D. R. Insulin-like growth factor-binding protein-3 proteolysis is induced after elective surgery. J. Clin. Endocrinol. Metab. 1992, 75, 590–595.

Fanayan, S.; Firth, S. M.; Butt, A. J.; Baxter, R. C. Growth inhibition by insulin-like growth factor-binding protein-3 in T47D breast cancer cells requires transforming growth factor-beta (TGF-beta) and the type II TGF-beta receptor. J. Biol. Chem. 2000, 275, 39146–39151.

Kansra, S.; Ewton, D. Z.; Wang, J.; Friedman, E. IGFBP-3 mediates TGF bet 1 proliferative response in colon cancer cells. Int. J. Cancer 2000, 87, 373–378.

Lee, S. W.; Gleason, N. R.; Stapleton, G. S.; Zhai, C.; Huang, E. H.; Bessler, M.; Whelan, R. L. Increased platelet-derived growth factor (PDGF) release after laparotomy stimulates systemic tumor growth in mice. Surg. Endosc. 2001, 15, 981–985.

Lee, S. W.; Gleason, N. R.; Southall, J. C.; Allendorf, J. D.; Blanco, I.; Huang, E. H et al. A serum-soluble factor(s) stimulates tumor growth following laparotomy in a murine model. Surg. Endosc. 2000, 14, 490–494.

Lee, S. W.; Southall, J. C.; Allendorf, J. D.; Bessler, M.; Whelan, R. L. Tumor proliferative index is higher in mice undergoing laparotomy vs. $CO_2$ pneumoperitoneum. Dis. Colon Rectum 1999, 42, 477–481.

Lee, S. W.; Gleason, N. R.; Ssenymanturo, K.; Woodring, J.; Bessler, M.; Whelan, R. L. Colon cancer tumor proliferative index is higher and tumor cell death rate is lower in mice undergoing laparotomy vs. insufflation. Surg. Endosc. 1998, 12, 514.

MacDonald, R. G.; Schaffer, B. S.; Kang, I. J.; Hong, S. M.; Kim, E. J.; Park, J. H. Growth inhibition and differentiation of the human colon carcinoma cell line, Caco-2, by constitutive expression of insulin-like growth factor binding protein-3. J. Gastroenterol. Hepatol. 1999, 14, 72–78.

Milsom, J. W.; Bohm, B.; Hammerhofer, K. A.; Fazio, V.; Steiger, E.; Elson, P. A prospective, randomized trial comparing laparoscopic versus conventional techniques in colorectal cancer surgery: a preliminary report. J. Am. Coll. Surg. 1998, 187, 46–54.

Murakami, K.; Matsuura, T.; Hasumura, S.; Nagamori, S.; Yamada, Y.; Saiki, I. Involvement of insulin-like growth factor binding protein-3 in the retinoic acid receptor-alpha-mediated inhibition of hepatocellular carcinoma cell proliferation. Cancer Lett. 2000, 151, 63–70.

Pidgeon, G. P.; Harmey, J. H.; Kay, E.; Da Costa, M.; Redmond, H. P.; Bouchier-Hayes, D. J. The role of endotoxin/lipopolysaccharide in surgically induced tumour growth in a murine model of metastatic disease. Br. J. Cancer 1999, 81, 1311–1317.

Rajah, R.; Valentinis, B.; Cohen, P. Insulin-like growth factor (IGF)-binding protein-3 induces apoptosis and mediates the effects of transforming growth factor-β1 on programmed cell death through a p53- and IGF-independent mechanism. *J. Biol. Chem.* 1997, 272, 12181–12188.

Robinson, J. R. Sustained and Controlled Release Drug Delivery Systems, ed., Marcel Dekker, Inc., New York, 1978.

Shiromizu, A.; Suematsu, T.; Yamaguchi, K; Shiraishi, N.; Adachi, Y.; Kitano, S. Effect of laparotomy and laparoscopy on the establishment of lung metastasis in a murine model. *Surgery* 2000, 128, 799–805.

Southall, J. C.; Lee, S. W.; Allendorf, J. D.; Bessler, M.; Whelan, R. L. Colon adenocarcinoma and B-16 melanoma grow larger following laparotomy vs. pneumoperitoneum in a murine model. *Dis. Colon Rectum* 1998, 41, 564–569.

Taylor, L. D., et al. *Nucl. Acids Res.* 1992, 20, 6287–6295.

Yu, H.; Rohan, T. Role of the Insulin-like Growth Factor family in cancer development and progression. Review *J. Natl. Cancer Inst.* 2000, 92, 1472–1489.

What is claimed is:

1. An improved surgical method which comprises surgically resecting a colon tumor from a human subject via open abdominal surgery and administering to the subject an amount of a composition comprising IGF-BP3 and a pharmaceutically acceptable carrier effective to inhibit metastasis of tumor cells released into the subject's blood circulation during the surgical resection of the colon tumor.

2. The method of claim 1, wherein the IGF-BP3 is recombinant IGF-BP3.

3. The method of claim 1, wherein the administration is oral, intravenous or transdermal.

4. The method of claim 3, wherein the administration is intravenous.

5. The method of claim 1, wherein the administration of IGF-BP3 is before the start of the surgical resection.

6. The method of claim 1, wherein the administration of IGF-BP3 is concurrent with the surgical resection.

7. The method of claim 1, wherein the administration of IGF-BP3 is after the completion of the surgical resection.

* * * * *